US012581367B2

(12) United States Patent
Müller et al.

(10) Patent No.: US 12,581,367 B2
(45) Date of Patent: Mar. 17, 2026

(54) MEDICAL SYSTEM WITH SELF-HEALING WIRELESS NETWORK OF SENSORS

(71) Applicant: RTX A/S, Nørresundby (DK)

(72) Inventors: Ilka Müller, Nørresundby (DK);
Christopher Meisner, Nørresundby (DK); Claus Krohn Vesterholt, Nørresundby (DK); Yash Singh, San Diego, CA (US)

(73) Assignee: RTX A/S, Norresundby (DK)

( * ) Notice: Subject to any disclaimer, the term of this patent is extended or adjusted under 35 U.S.C. 154(b) by 930 days.

(21) Appl. No.: 17/613,345

(22) PCT Filed: May 6, 2020

(86) PCT No.: PCT/DK2020/050134
§ 371 (c)(1),
(2) Date: Nov. 22, 2021

(87) PCT Pub. No.: WO2020/233759
PCT Pub. Date: Nov. 26, 2020

(65) Prior Publication Data
US 2022/0312273 A1      Sep. 29, 2022

Related U.S. Application Data

(60) Provisional application No. 62/979,136, filed on Feb. 20, 2020.

(30) Foreign Application Priority Data

May 22, 2019      (DK) ........................... PA 2019 70326

(51) Int. Cl.
H04W 28/18      (2009.01)
G16H 40/67      (2018.01)
(Continued)

(52) U.S. Cl.
CPC ............ H04W 28/18 (2013.01); G16H 40/67 (2018.01); G16H 50/30 (2018.01); H04W 56/001 (2013.01); *H04W 84/18* (2013.01)

(58) Field of Classification Search
CPC ..... H04W 28/18; H04W 28/02; H04W 28/16; H04W 56/001; H04W 56/002;
(Continued)

(56) References Cited

U.S. PATENT DOCUMENTS 5,995,500 A      11/1999   Ma et al.
7,359,950 B2 *   4/2008    Choi ..................... H04W 84/20
                                                                  709/208
(Continued)

FOREIGN PATENT DOCUMENTS

CN      101551849 A    10/2009
CN      102833307 A    12/2012
(Continued)

OTHER PUBLICATIONS

International Patent Application No. PCT/DK2020/050134; Int'l Search Report and the Written Opinion; dated Jul. 14, 2020; 17 pages.
(Continued)

*Primary Examiner* — Un C Cho
*Assistant Examiner* — Rasha K Fayed
(74) *Attorney, Agent, or Firm* — BakerHostetler

(57)      ABSTRACT

A wireless sensor device for wireless transmission of sensed medical data to a medical monitoring and/or intervention device. The sensor device has a sensor element for sensing a physical parameter related to a body of a living person or animal. A wireless RF transmitter and receiver serves to transmit data packets with the sensed physical parameter, and to also receive data packets, in accordance with a TDMA based network protocol. A processor system controls
(Continued)

operation of the wireless RF transmitter and receiver, including that the sensor device can operate as wireless RF synchronization master or slave, and the sensor device can negotiate according to a deterministic negotiation algorithm to appoint one of a plurality of wireless RF devices connected to the TDMA based network as wireless RF synchronization master, if it is detected that no master is available. This allows a self-healing network, since one of a number of slave devices present in the network session can be appointed as a new master, thus even though the master device becomes out of range or is switched off. This provides a reliable and low latency wireless RF network for medical system, e.g. for a Continuous Positive Air Pressure device (CPAP) which can use sensed data from one or more sensor device to control its air blower to provide an appropriate air pressure.

14 Claims, 4 Drawing Sheets

(51) Int. Cl.

| | | |
|---|---|---|
| *G16H 50/30* | (2018.01) | |
| *H04W 56/00* | (2009.01) | |
| *H04W 84/18* | (2009.01) | |

(58) Field of Classification Search
CPC . H04W 56/0015; H04W 84/18; H04W 84/08; H04W 84/20; H04W 84/02; H04W 4/08; H04W 4/70; H04W 4/023; H04W 4/00; H04W 4/02; H04W 88/06; H04W 88/02; H04W 88/08; H04W 72/542; H04W 72/1215; H04W 72/0406; H04W 72/04; H04W 72/12; H04W 72/082; H04W 72/085; H04W 8/005; H04W 76/14; H04W 76/00; H04W 40/04; H04W 40/00; H04W 8/00; H04W 92/00; H04W 74/00; H04W 74/0808; H04W 48/00; H04W 52/0209; H04W 52/243; H04W 16/00; H04W 16/14; H04W 16/22; H04W 16/04; H04W 16/24; H04W 24/00; H04L 67/104; H04L 67/12; H04L 41/00; H04L 12/00; H04L 5/003; H04B 17/18; H04B 17/20; H04B 1/715; H04B 7/2621; Y02D 30/70; Y02B 60/50; G16H 40/67; G16H 50/30
See application file for complete search history.

(56) References Cited

U.S. PATENT DOCUMENTS

| | | | | |
|---|---|---|---|---|
| 7,942,824 | B1 * | 5/2011 | Kayyali | A61B 5/08 |
| | | | | 128/204.26 |
| 9,789,273 | B2 * | 10/2017 | Lucci | A61M 16/203 |
| 10,118,009 | B2 | 11/2018 | Darkin | |
| 2002/0031100 | A1 * | 3/2002 | Sashihara | H04L 1/0001 |
| | | | | 370/294 |
| 2002/0055978 | A1 * | 5/2002 | Joon-Bo | H04W 84/20 |
| | | | | 709/209 |
| 2002/0072329 | A1 * | 6/2002 | Bandeira | H04B 7/2609 |
| | | | | 455/25 |
| 2006/0030318 | A1 * | 2/2006 | Moore | H04W 48/16 |
| | | | | 455/434 |
| 2006/0194611 | A1 | 8/2006 | Pasternak | |
| 2010/0027517 | A1 * | 2/2010 | Bonta | H04L 47/745 |
| | | | | 370/338 |
| 2011/0039554 | A1 * | 2/2011 | Bims | H04L 1/0033 |
| | | | | 455/434 |
| 2011/0294474 | A1 * | 12/2011 | Barany | H04W 8/005 |
| | | | | 455/414.1 |
| 2012/0084342 | A1 | 4/2012 | Brown et al. | |
| 2012/0202484 | A1 | 8/2012 | Dickinson et al. | |
| 2013/0132500 | A1 * | 5/2013 | Vandwalle | H04L 67/1051 |
| | | | | 709/208 |
| 2013/0137422 | A1 | 5/2013 | Sugitani | |
| 2013/0273948 | A1 * | 10/2013 | Tel-Or | H04W 88/06 |
| | | | | 455/500 |
| 2014/0335853 | A1 * | 11/2014 | Sartori | H04W 56/002 |
| | | | | 455/552.1 |
| 2015/0072702 | A1 * | 3/2015 | Chun | H04W 4/08 |
| | | | | 455/454 |
| 2015/0365168 | A1 * | 12/2015 | Arimura | H04W 56/0015 |
| | | | | 398/52 |
| 2016/0134433 | A1 * | 5/2016 | Youngbull | H04L 45/16 |
| | | | | 370/347 |
| 2017/0289959 | A1 * | 10/2017 | Aki | H04W 72/0453 |
| 2019/0030275 | A1 * | 1/2019 | Darkin | A61M 16/06 |
| 2019/0232047 | A1 * | 8/2019 | Chu | A61H 23/00 |
| 2020/0294401 | A1 * | 9/2020 | Kerecsen | G08G 1/205 |
| 2022/0391867 | A1 * | 12/2022 | Glaser | G06F 3/017 |

FOREIGN PATENT DOCUMENTS

| | | |
|---|---|---|
| CN | 108370389 A | 8/2018 |
| JP | 2016-167647 A | 9/2016 |

OTHER PUBLICATIONS

Nie et al.; "A statistical frame based TDMA protocol for human body communication"; BioMed Engineering Online; vol. 14:65; 2015; 20 pages.

"Time-division multiple access"; Wikipedia; https://en.wikipedia.org/w/index.php?title=Time-division_multiple_access&oldid=894129451; May 26, 2020; accessed Dec. 6, 2020; 4 pages.

Lien et al.; "Design of P2Pnet: An Autonomous P2P Ad-Hoc Group Communication System"; Dept. of Computer Science, Nat'l Chengchi University; Conference Paper; Jun. 2009; 7 pages.

Petig et al.; "Self-stabilizing TDMA Algorithms for Wireless Ad-hoc Networks without External Reference"; 13th Annual Mediterranean Ad Hoc Networking Workshop; 2014; p. 87-94.

Santos et al.; "Self-configuration of an Adaptive TDMA wireless communication protocol for teams of mobile robots"; IEEE Int'l Conf. on Emerging Technologies and Factory Automation; 2008; p. 1197-1204.

"Titan Dect Solutions—Multicom Headsets and belt boxes"; Titan Communication Systems; 2 pages.

Non-Final Office Action dated Dec. 5, 2023, issued in corresponding U.S. Appl. No. 17/613,319.

International Search Report and Written Opinion dated Oct. 16, 2020, issued in corresponding International Application No. PCT/DK2020/050131.

* cited by examiner

MEDICAL SYSTEM WITH SELF-HEALING WIRELESS NETWORK OF SENSORS

CROSS-REFERENCE TO RELATED APPLICATIONS

This application is the National Stage of International Patent Application No. PCT/DK2020/050134, filed May 6, 2020, which claims the benefit of Danish application number PA 2019 70326, filed May 22, 2019 and U.S. application No. 62/979,136, filed Feb. 20, 2020, the entireties of which foregoing applications are incorporated herein by reference in their entireties for any and all purposes.

FIELD OF THE INVENTION

The present invention relates to the field of medical devices or medical systems, such as medical therapy devices. Specifically, the invention provides a medical system and a method for providing a self-healing wireless network of sensors for measuring physical parameters related to a body of a person or an animal, e.g. body vital parameters or physical parameters related to a medical therapy of the body.

BACKGROUND OF THE INVENTION

In typical medical systems, e.g. involving a medical therapy devices in homecare or in a hospital, a number of relevant physical parameters are often monitored for a patient. Either wired sensors are used, or wireless RF sensors may be used. However, in both cases, a complicated setup may be required. In a typical wireless sensor based system, e.g. a Continuous Positive Air Pressure (CPAP) system, a number of wireless sensors may provide input for control of the CPAP blower. However, the entire system may need to be setup specifically for the actual types of wireless sensors connected to the system, and if a sensor is added or removed, the CPAP system may need to be reconfigured.

In CPAP systems, it is a problem to accurately control the air blower to provide a precise forced airflow profile and duration to match the patient's condition.

Specifically, it is a problem to provide a CPAP system which can provide pre-emptive data to spin up the blower and generate a gas pressure wave in anticipation of the next respiratory cycle. Furthermore, the CPAP system should still be simple to setup and use for medical personnel or even for an untrained person, e.g. a sleep Apnea CPAP system for home use.

Intensive care ventilator devices are typically complex devices capable of being controlled in response to a high number of medical sensor inputs. Thus, such device require specially trained persons to perform a complicated setup procedure involving a substantial start-up time before intensive care can begin for treatment of a breathing disabled patient.

Thus, it is a problem to provide a medical system which is flexible with respect to addition of removal of sensors, and which is still easy to use or setup, even for an untrained person.

SUMMARY OF THE INVENTION

Thus, according to the above description, it is an object of the present invention to provide a solution to problems related to wireless sensors in medical systems which are complicated to setup, not flexible with respect to adding sensors and lack fault tolerance.

In a first aspect, the invention provides a sensor device comprising at least one sensor element arranged to sense a physical parameter related to a body of a living person or animal or related to a medical therapy performed on the body, a wireless RF transmitter arranged to transmit data packets indicative of the sensed physical parameter represented in an RF signal in accordance with a TDMA based network protocol, a wireless RF receiver arranged to receive data packets represented in an RF signal in accordance with the TDMA based network protocol, and a processor system connected to control operation of the wireless RF transmitter and receiver according to the TDMA based network protocol, comprising being configured to operate as a wireless RF synchronization master or a wireless RF synchronization slave, and arranged to communicate with other wireless RF devices connected to the TDMA based network via the wireless RF receiver and transmitter, and to negotiate with other wireless RF devices, whether to operate as a wireless RF synchronization master or a wireless RF synchronization slave, wherein said negotiation comprises a deterministic negotiation algorithm serving to appoint one of a plurality of wireless RF devices connected to the TDMA based network as wireless RF synchronization master, and wherein the negotiation algorithm causes devices connected to the TDMA based network to initiate a negotiation for appointing a new wireless RF synchronization master in case it is detected, that no wireless RF synchronization master is available in the TDMA based network session.

Such sensor device is advantageous since it can form part of self-healing fault-tolerant wireless network for a medical system. With multiple sensor devices connected in a wireless network along with a medical device receiving physical parameter data from the sensor devices, a flexible and easy to use system is provided. Especially, the network is flexible, since the negotiation algorithm allows sensor devices to enter or leave the network without any manual interaction of a user. Thus, in a medical context sensor devices can be added for providing extra medical data input without any setup procedure required. E.g. the medical device receiving the input data can be programmed to perform different control algorithms in case only a limited number of input data are available from the sensor device network, while another control algorithm can be chosen automatically if more become sensor devices are added. The same applies if sensor devices are removed from the network, e.g. due to damage, or due to being moved out of wireless range. This provides a fault tolerant system, since even if the RF synchronization master is unavailable, the remaining participants in the network session will continue after appointing a new RF synchronization master. This provides a high degree of flexibility, and still allows an easy to use fully automated setup procedure or fully automated operation without any skilled personnel.

The wireless network supported by the sensor device is capable of providing physical parameter data with a low latency, thus allowing for timing critical inputs to a medical therapy device etc. Further, the network allows local decisions to be performed by one or a group of sensor devices, thereby supporting a fast medical decision or alarm to be communicated to a medical therapy device in case a critical event is detected by one or more sensor devices. By adding a sensor device, e.g. for measuring a body vital parameter of a critical patient, the sensor device can immediately transmit data on the network, thus ensuring easy and a low access time for adding a new sensor device to a medical system network.

Even further, a high flexibility is provided, since the network allows sensor devices to autonomously determine and communicate a sample rate for the data packets depending on the data update rate. This allows a good utilization of the available bandwidth on the network by ensuring that network capacity is spent on sensor devices producing real-time data, e.g. a vital pressure sensor, and require a high priority channel for data transfer. On the other hand, e.g. a temperature sensor may only be required to send a simple temperature value every 10 seconds or the like. The payload structure in the frame format is sufficiently flexible to allow scalability and automatic on and off boarding of a sensor without affecting the latency or aggregate throughput of the system.

The sensor device is further flexible due to the self-healing principle. Especially, it allows division of a group of sensor devices into sub-groups, or sub-groups may be joined to form a larger group of sensor devices. The master role is negotiated to ensure only one master for timing synchronization, and redundant masters will change to slave operation. Further, the network will allow two sensor devices operating as synchronization slaves to communicate directly without requiring communication relay by a master device. Still further, the network protocol supports that a group of sensor devices can all receive data packets from one sensor device, or from a medical device on the network. This may be advantageous in a medical setup, e.g. for transmitting a communication to all sensor devices in the network from a medical device, e.g. to cause the sensor devices to change its mode of operation with respect to sensing of the physical parameter data, e.g. to enter an emergency mode of operation with a higher update rate of the physical parameters.

The below phrases will be used and are therefore explained:

Time Division Multiple Access (TDMA).

Received Signal Strength Indicator (RSSI).

Cyclic Redundancy Check (CRC) for error check and possible correction of data.

Error Correction Code (ECC).

A single radio event e.g. transmit or receive is denoted a slot or time slot.

A repeated sequence of downlink and uplink slots, including slot(s) for interference scanning (TDMA frame) is denoted a frame.

In the following preferred embodiments and features will be described.

Preferably, the deterministic negotiation algorithm causes the sensor device, if operating as a wireless RF synchronization master, to negotiate with one or more other wireless RF devices connected to the TDMA based network also operating as wireless RF synchronization master, so as to appoint only one wireless RF device to continue to operate as a wireless RF synchronization master, whereas the remaining wireless RF devices will switch to wireless RF synchronization slave operation. This solves the problem of joining two RF synchronization master devices in a network session. This may occur e.g. if a wireless RF device programmed to default operate as RF Synchronization master enters and on-going network session already having an RF synchronization master appointed. Further, this allows two groups of RF devices, each with one RF synchronization master, to be joined into one network session with one common RF synchronization master.

If preferred, payload size may be configured automatically on addition of an RF Synchronization master or slave.

It may be preferred that the processor system is programmed to operate as a wireless RF synchronization slave as a default mode of operation when entering a wireless TDMA network session. Such default setting as slave device allows the sensor device to easily enter an on-going network session with an already appointed RF synchronization master.

In some embodiment, the sensor device is arranged to sense body vital parameter data for the living person or animal.

In some embodiments, the physical parameter data comprises one or more of: heart rate, blood pressure, blood oxygen saturation, abdominal movement, thoracic movement, leg movement, snore sound, body temperature, perspiration humidity, carbon dioxide exhalation, and tremor of a body part. Thus, the sensor device is suitable for combination with known sensor elements to allow sensing of one or more of the above into a compact stand-alone self-powered device which is easy to pick up, mount in relation to the body of the person or animal, to switch on, and wherein the sensor device then automatically enters an on-going wireless TDMA network session for immediate transmission of sensed physical parameter data.

In a specific example, the sensor device may be integrated into the mask of a Positive Air Pressure (PAP) system, wherein the air pressure and/or humidity in the mask can be sensed and be wirelessly transmitted for use in the control of an air blower in the PAP device.

In some embodiments, the physical parameter data comprises one or more therapy relevant parameter data related to a medical intervention or therapy of the body. Such data may be related to sensing of e.g. an air pressure or a light or an electric signal or the like to be applied to the body.

Especially, the physical parameter data may comprise one or more of: an airflow pressure, an airflow rate, a temperature, a moisture or humidity measure, a measure of a gas mixture.

In some embodiments, the sensor device is programmed to process a sensed physical parameter sensed by the sensor element according to a decision algorithm in order to determine a decision in response to the sensed physical parameter, and wherein the sensor device is arranged to transmit data indicative of said decision represented in an RF signal via the TDMA based network. Thus, in such embodiments, the sensor device has processing power to determine a local decision based on sensed data, e.g. a sensor device integrated in the mask of a PAP system, which may determine air pressure and/or humidity in the mask and determine a decision to be communicated immediately to the controller of the air blower to adapt the applied air pressure. Especially, the sensor device may be arranged to receive an RF signal from one or more wireless RF devices connected to the wireless TDMA based network and to receive further physical parameter data represented therein, and to process said received further physical parameter data according to the decision algorithm to determine the decision in response thereto. This allows a group of different sensor devices to cooperate to provide a local decision based on sensed physical parameters within the group.

In some embodiments, the sensor device is arranged to communicate a sample rate for the physical parameter data in the data packets. Especially, the sample rate may be determined depending on a rate of update of the physical parameter data. This allows a high flexibility and a high degree of utilization of the wireless RF capacity, since each sensor device can determine an individual sample rate and rate of update, e.g. dynamically in accordance with its own decision or in accordance with a command received over the wireless TDMA based network from a medical device. This accommodates connection of sensor devices with a variety of required wireless RF bandwidth demands, e.g. ranging from sensor devices transmitting a single value at a low rate, up to sensor devices sensing and communicating time series of data sampled at a high sample rate, e.g. such as EEG or ECG time signals.

In preferred embodiments, the sensor device is programmed to support multiple RF frequencies or channels. Especially, the sensor device may be programmed to scan between at least a limited set of said multiple supported RF frequencies or channels so as to detect wireless RF signals from other wireless RF devices present within wireless range. More specifically, the sensor device may be programmed to determine an interference level, e.g. an RSSI, for each of the at least limited set of the multiple supported RF frequencies or channels. This allows the sensor devices to select the RF frequency or channel which is available for communicating the physical parameter data with the minimal disturbance from other wireless RF traffic. Especially, the sensor device may be programmed to determine a measure of packet error rates for each of the at least limited set of multiple supported RF frequencies, and to select on which RF frequency to transmit data packets indicative of the sensed physical parameter accordingly. Further, interference level and packet error rate can be used to determine which RF frequencies or time slots to use. Alternatively, or additionally, this can be used in the negotiation between a plurality of wireless RF devices which one to operate as wireless RF synchronization master, since it is preferred that the RF synchronization master is the one RF device which provides the most stable RF communication to the remaining RF devices within wireless range.

To provide redundant data transmission, the sensor device may be programmed to transmit a data packet indicative of the sensed physical parameter on at least two different supported RF frequencies or channels and/or in two different time slots so as to provide redundant transmission of data packets. Especially, the sensor device may be programmed to select which one or more of the multiple supported RF frequency to be used for transmission of data packet indicative of the sensed physical parameter in response to a combination of two or more of:

1) levels of RF activity at the supported RF frequencies or channels,
2) reported measurement data from one or more other wireless RF devices indicative of channel quality indicator values measured for a plurality of the supported RF frequencies or channels,
3) a frequency distance between a currently used RF frequency or channel, and another one or more supported RF frequency or channel, and
4) a measure of packet error rates collected for at least a limited set of the multiple supported RF frequencies or channels.

Alternatively, or additionally, a combination of two or more of the mentioned 1)-4) can be used in the negotiation between wireless RF devices which one to operate as a wireless RF synchronization master.

The supported RF frequencies or channels may specifically have RF bearers located within a frequency range of less than 100 MHz, e.g. less than 20 MHz.

In some embodiments, the sensor device is programmed to perform scanning and transmission of data packet indicative of the sensed physical parameter at selected time slots. The sensor device may be programmed to negotiate with other wireless RF devices to perform transmission of data packet indicative of the sensed physical parameter in different time slots.

In some embodiments, the sensor device is programmed to provide, in each time slot, a CRC error check field. Specifically, a seeding of the CRC may be used as a hidden system identification, which can allow discrimination between data packets originating from separate wireless TDMA networks.

The sensor device is preferably programmed to form a participate in a group comprising a wireless RF device operating as wireless RF synchronization master and one or more wireless RF devices operating as wireless RF synchronization slaves. This allows e.g. the sensor device to form a group along with one or more other sensor devices which can communicate physical parameter data and form a group local decision based thereon.

The sensor device is preferably programmed to detect frame timing of incoming wireless RF signals and to align frame timing of wireless RF signals transmitted according to the detected frame timing.

The sensor device may be programmed to support a plurality of different sampling rates for wireless RF transmission of the physical parameter data. This can be used for different modes of operation where e.g. different update rates of the sensed physical parameter is required. E.g. that may be a "slow" mode of operation with update of the sensed physical parameter at a low pace, a "normal" mode of operation with a medium update rate, and an "emergency" mode of operation with a high update rate. Especially, the sensor device may be programmed to receive a command with the wireless TDMA based network to select one of the plurality of different sampling rates, or it may be programmed to autonomously select the sampling rate.

The sensor device may be programmed to support a plurality of different data payload sizes for wireless RF transmission of the physical parameter data.

In some embodiments, the sensor device is programmed to, when appointed as wireless RF synchronization master, to have special properties, especially it may be programmed to one or more of:
  to impose TDMA frame structure and timing constraints of the TDMA based network;
  to determine at least time synchronization of the TDMA frame structure;
  to determine one or more of: RF channel assignment, RF transmission power, total number of wireless RF synchronization slaves, RF frequency assignment, modulation format, ECC mode, payload, control data per, and power control;
  to transmit wireless RF data 10-40% of time, preferably 20-30% of time, and to receive wireless RF data in the remaining time;
  to determine a sub-division of a TDMA frame into time slots of a duration of 2-10 ms, e.g. 3-8 ms, preferably 4-6 ms;
  to determine a sub-division of the TDMA frame into 4-10 time slots, depending on modulation rate and frame size;

to transmit in the first time slot in each TDMA frame information indicative of a channel condition and channel availability;

The sensor device may be programmed to transmit data packets with a duration of 0.1-10 ms, e.g. 0.5-2 ms, preferably 0.8-1.2 ms. E.g. the sensor device may be programmed to receive information via the wireless TDMA based network to select a specific data packet duration for the transmission of data packets. In other embodiments, the sensor device is programmed to transmit data packets with a fixed duration.

The sensor device may be programmed to allow for wireless TDMA based network synchronization of all of: slot, symbol and RF carrier.

The sensor device may have an RF receiver and/or transmitter comprising two or more different RF antennas for receipt and/or transmission of RF signals, e.g. to allow antenna diversity to further increase communication range and transmission reliability.

In some embodiments, the TDMA based network may be implemented based on a Digital Enhanced Cordless Telecommunication compatible protocol.

It is to be understood that the required RF transmitter and RF receiver circuits, antenna and programming required to implement the described wireless TDMA network properties will be known by the skilled person based on the present description of the inventive method.

In a second aspect, the invention provides a medical system comprising at least one sensor device according to the first aspect,
a medical device comprising
at least one medical therapy unit arranged to provide one or both of: medical active monitoring, and medical intervention of a living person or animal,
a wireless RF receiver arranged to receive data packets represented in an RF signal in accordance with a TDMA based network protocol, so as to allow receipt of data packets with physical parameter data from the at least one sensor device,
a processor system connected to the wireless RF receiver and programmed to operate according to the TDMA based network protocol, and
wherein the processor system is connected to the medical therapy unit so as to control at least one parameter of the medical therapy unit in order to cause the medical therapy unit to adapt the provided medical active monitoring or medical intervention in response to received physical parameter data from the at least one wireless sensor device.

This allows a flexible system of wireless sensor devices to deliver measured physical parameter data to control the medical device.

Especially, the medical device may be configured for controlling the at least one parameter of the medical therapy unit according to a selectable control algorithm which allows control of the medical therapy unit in response to the number and types of physical parameter data available from sensor devices. One control algorithm may be selected in case only few physical parameter data are available, and if more sensor devices are added to the wireless TDMA based network, another control algorithm may be selected in order to take advantage of the further data available to allow improved control of the medical therapy unit.

In preferred embodiments, the medical device further comprises a wireless RF transmitter arranged to transmit data packets represented in an RF signal in accordance with said TDMA based network protocol, and wherein the processor system of the medical device is connected to the wireless RF transmitter and being programmed to operate according to said TDMA based network protocol and said negotiation algorithm. This allows the medical device to communicate wirelessly with connected sensor devices via the network. Especially, the processor system of the medical device may be programmed to operate as a wireless RF synchronization master as a default. The medical device may be programmed to transmit commands to the sensor device (s) via the wireless TDMA based network, e.g. to request a specific update rate of the transmitted physical parameter data.

In preferred embodiments, the system comprises a plurality of sensor devices according to the first aspect, e.g. 2-10 or even more sensor devices. Preferably, at least two of the plurality of sensor devices have different types of sensor element arranged to sense different physical parameters. In some embodiments, at least one sensor device comprises a sensor element arranged to sense at least one body vital parameter of the person or animal.

In a specific embodiment, the medical device comprises an Adaptive Positive Air Pressure (APAP) device or a Continuous Positive Air Pressure (CPAP) device comprising a controllable air blower for delivering a controllable pressurized air to an airway of the living person or animal. Specifically, the medical device is arranged to receive physical parameter data from the at least one sensor device, and to determine a control output to the controllable air blower accordingly, so as to adapt delivered pressurized air to the airway of the living person or animal in accordance with the sensed physical parameter data. Especially, the medical device may be arranged to deliver a controllable mix of at least two different gases to the living person or animal, and wherein the medical device is arranged to determine a mix of gases in response to sensed physical parameter data from the at least one sensor device and to control the controllable mix of the at least two different gases accordingly. Specifically, at least one sensor device may be positioned in or on a mask connected to deliver pressurized air to the airway of the living person or animal. More specifically, said sensor device is arranged to sense at least one of: humidity and pressure inside the mask, and wherein the medical device is arranged to control the controllable air blower in response to received data indicative of the sensed at least one of: humidity and pressure inside the mask. Said at least one sensor device may comprise a sensor element arranged to sense a physical parameter indicative of position a person's head, and wherein the medical device is arranged to control the controllable air blower in response to received data indicative of position of the person's head. Said at least one sensor device may comprise a sensor element arranged to sense a physical parameter indicative of snore sound from the person, and wherein the medical device is arranged to control the controllable air blower in response to received data indicative of the snore sound from the person.

In some embodiments, at least one sensor device is programmed to process a sensed physical parameter sensed by the sensor element according to a decision algorithm in order to determine a decision in response to the sensed physical parameter and to transmit data indicative of said decision represented in an RF signal via the TDMA based network, wherein the medical device is arranged to receive said data indicative of said decision from the sensor device, and to control at least one parameter of the medical therapy unit accordingly. This allows one or more sensor devices to cooperate in determining a local decision based on at least one physical parameter, e.g. based on sensor devices in or on a mask of an APAP or a CPAP system. This allows a fast decision which may be important in case of a critical event which is detected locally, and which is transmitted with low latency to the medical device which can take action accordingly without the need to perform itself complicated processing of data from the sensor device(s) to arrive at the decision itself. Specifically, said decision determined locally, may comprise an alarm, wherein the sensor device is arranged to decide to transmit an alarm in case the sensor device senses a physical parameter, e.g. a body vital parameter, which is outside a predetermined interval.

Especially, the medical device may comprise at least one of: a PAP device to apply to an airway of the living person or animal, a cardiac defibrillator, an active prosthetic, a robotic surgery device. However, it is to be understood that the invention is applicable within many additional applications.

In some embodiments, the medical system comprises a ventilator device (or a respirator device) arranged to provide air to an airway of the living person or animal the in an automatic cycle or a semi-automatic cycle. Especially, such ventilator device may be an intensive care ventilator device for assisting or completely take over breathing of a living person or animal. In some embodiments, such ventilator device is prepared for connection to a number of wireless sensor devices for providing medical data as input for control of parameters of the semi-automatic or automatic breathing pattern provided to the living person or animal, e.g. the ventilator device may be capable of applying a selectable ratio of oxygen to the air provided to the living person or animal. In intensive care, time required for setup of a ventilator device for treatment of a breathing disabled patient can be critical. The ventilator device according to the present invention allows a quick setup time, since the ventilator device can be programmed to function for automatic connection of which wireless sensor devices that are available, so as to allow a prompt start of a breathing assist, also on ventilator device that may be prepared for a complex control in response to a large number of different sensor inputs. E.g. the ventilator device may be programmed for a start-up sequence involving automatically connecting available wireless sensor devices.

Especially, the ventilator device may be arranged to adapt one or more of: air pressure, oxygen ratio, respiratory frequency, respiratory depth, and air pressure versus time profile, in response to received physical parameter data from the at least one wireless sensor device. Especially, the ventilator device may be arranged to adapt a ration of oxygen supplied to the air provided to the airway of the person or animal in response to received physical parameter data from the at least one wireless sensor device. Especially, the ventilator device may be arranged to select a parameter comprising one or more of: a respiratory frequency, a respiratory depth, and an air pressure profile versus time.

The ventilator device may be an intensive care ventilator device arranged to provide air to an airway of the living person or animal, e.g. being arranged to provide air to an airway of the living person or animal in an automatic cycle to assist or take over breathing cycles of a breathing disabled person or animal.

In a third aspect, the invention provides a method for controlling a medical device, the method comprising providing at least one sensor device according to the first aspect, providing a medical device arranged to provide medical active monitoring or medical intervention of a living person or animal, the medical device further comprising a wireless RF receiver arranged to receive data packets represented in an RF signal in accordance with a TDMA based network protocol, establishing a wireless TDMA based network session between the at least one sensor device and the medical device, transmitting, from the at least one sensor device, a data packet indicative of a sensed physical parameter represented in a wireless RF signal in accordance with the TDMA based network protocol, receiving, by the medical device, the wireless RF signal and determining the physical parameter represented therein, and adapting at least one parameter of the medical active monitoring or medical intervention in response to the received physical parameter.

In some embodiments, the method comprises processing, by the at least one sensor device, the sensed physical parameter, and determining a decision based accordingly, transmitting, from the sensor device, a data packet indicative of the decision represented in a wireless RF signal in accordance with the TDMA based network protocol, receiving, by the medical device, the wireless RF signal and determining the decision represented therein, and adapting at least one parameter of the medical active monitoring or medical intervention in response to the received decision.

In a fourth aspect, the invention provides a computer program product comprising program code arranged to cause, when executed on a sensor device with a processor and on a medical device with a processor, to perform the method according to the third aspect.

In a fifth aspect, the invention provides use of the sensor device according to the first aspect for a medical application for surveillance or therapy of a person or animal, e.g. in a hospital, in an ambulance or in a homecare.

In a sixth aspect, the invention provides use of the medical system according to the second aspect for a medical application for surveillance or therapy of a person or animal, e.g. in a hospital, in an ambulance or in a homecare.

It is appreciated that the same advantages and embodiments described for the first aspect apply as well the further mentioned aspects. Further, it is appreciated that the described features and embodiments can be intermixed in any way between all of the mentioned aspects.

BRIEF DESCRIPTION OF THE FIGURES

The invention will now be described in more detail with regard to the accompanying figures of which

The figures illustrate specific ways of implementing the present invention and are not to be construed as being limiting to other possible embodiments falling within the scope of the attached claim set.

DETAILED DESCRIPTION OF THE INVENTION

Figure 1:
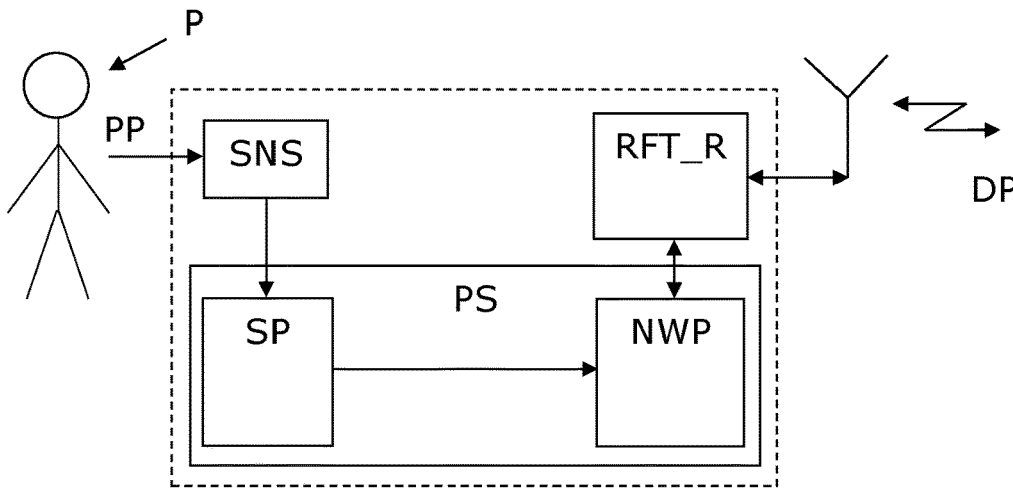
FIG. 1 illustrates a block diagram of a sensor device embodiment.

FIG. 1 illustrates a wireless sensor device embodiment for a medical application with a patient P under medical therapy or monitoring, and the sensor device has a sensor element SNS arranged to sense a physical parameter PP related to the medical condition of the patient, e.g. blood pressure, blood oxygen saturation, temperature or the like, on the patient P. The sensor device is controlled by a processor system PS, which includes a signal processing SP serving to process a signal from the sensor element SNS, e.g. involving sampling and analog-to-digital conversion of an analog electric signal from the sensor element SNS, and splitting data into suitable data packets for wireless transmission.

The sensor device has a wireless RF transmitter and receiver unit RFT_R arranged to transmit data packets DP indicative of the sensed physical parameter PP represented in an RF signal in accordance with a TDMA based network protocol NWP. The RF transmitter and receiver unit RFT_R is further arranged to receive data packets represented in an RF signal in accordance with the TDMA based network protocol, e.g. commands from a medical device, or data packets with sensed physical parameter data from other sensor devices.

The processor system controls operation of the wireless RF transmitter and receiver unit RFT_R according to the TDMA based network protocol NWP which is a self-healing fault tolerant wireless network capable of delivering data packets with a low latency. These features of the TDMA based network protocol will be described in more details in the following. This network protocol allows the sensor device to connect to a medical device for delivering sensor data for control of a medical device, e.g. a device for monitoring or for providing a therapy to a patient, or a device being a combination of monitoring and providing therapy. The sensor device is flexible and easy to use, since the TDMA based network protocol allows automatic connection to a network session as soon as the sensor device is switched on. Thus, in a medical setup, further medical sensor devices can easily added, if required by the medical patient, without any complicated manual network connection setup. A medical device connected to the network can thus quickly gain access to sensed data from a newly installed sensor device, and thus adapt its monitoring and/or therapy accordingly. Such easy and fast setup can be important for a medical emergency setting, where many sensing parameters may be required for correct treatment of incoming critical patients in an ambulance or in an emergency clinic at a hospital. In a medical homecare setup, the sensor device is suitable for easy connection to a homecare medical therapy device by an untrained user.

Figure 2:
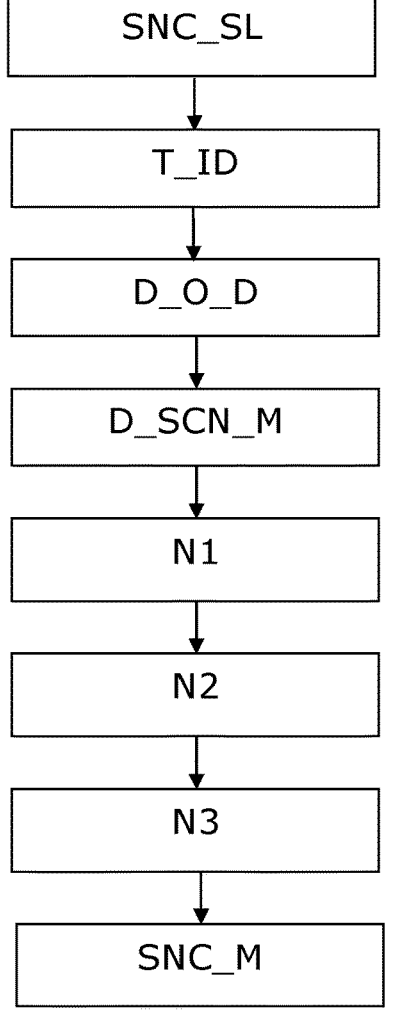
FIG. 2 illustrates steps of a preferred wireless TDMA based self-healing network protocol.

FIG. 2 illustrates basic steps of a preferred wireless TDMA network protocol embodiment to be implemented and performed by the processor system PS the sensor device. The processor system PS is arranged to control the wireless RF transmitter and receiver unit RFT_R to operate as a wireless RF synchronization master or a wireless RF synchronization slave in a wireless TDMA network session. The processor system PS is further configured for two-way communication with other wireless RF devices connected to the TDMA based network via the wireless RF transmitter and receiver unit RFT_R. This enables the sensor device to negotiate with other wireless RF devices, whether to operate as a wireless RF synchronization master or a wireless RF synchronization slave.

The negotiation with other wireless RF devices in the TDMA network session is a deterministic negotiation algorithm serving to appoint one of a plurality of wireless RF devices connected to the TDMA based network as wireless RF synchronization master. The first step of the protocol embodiment in FIG. 2 is to set as default to operate as wireless RF synchronization slave SNC_SL. Next, transmitting T_ID a signal at a predefined RF carrier frequency and other to identify the presence of the sensor device on the network. Next, step is a step of detecting other devices on the network D_O_D. Next, step is to detect if a wireless RF synchronization master D_SCN_M is present among identified RF devices on the network. In case it is detected that no wireless RF synchronization master is available in the TDMA based network session, a deterministic negotiation algorithm for appointing one RF device as a new wireless RF synchronization master starts. A first step N1 of such negotiation is to transmit and receive messages to and from other RF devices in the network session, preferably based on measuring RF signal quality parameters for RF signals received from other devices, e.g. RSSI and/or a measure of data packet error rate. Next step N2 to determine according to a deterministic score algorithm a value for each device in the network session, and next N3 appointing the new wireless RF synchronization master in response to the value from the deterministic score algorithm, e.g. the RF device with the highest score value based on the score algorithm which calculates a weighted result for the overall transmitting and receiving signal quality, thus appointing the most reliable RF device as the new RF synchronization master. Finally, the sensor device is programmed to switch from RF synchronization slave to RF synchronization master operation SNC_M, in case it is appointed in the negotiation procedure N1-N3.

The described protocol will ensure that a wireless RF synchronization master will always be appointed, and that only one single device is appointed due to the deterministic score algorithm. This is important, e.g. if the present wireless RF synchronization master is moved out of range or switched off. Thus, in this way the TDMA based network is self-healing and fault tolerant.

Preferably, the deterministic negotiation algorithm further involves causing the sensor device, if operating as a wireless RF synchronization master, to negotiate with one or more other wireless RF devices connected to the TDMA based network also operating as wireless RF synchronization master, so as to appoint only one wireless RF device to continue to operate as a wireless RF synchronization master, whereas the remaining wireless RF devices will switch to wireless RF synchronization slave operation. Hereby, the joining of groups of RF devices to form one network session is possible without ambiguity with respect to wireless RF synchronization.

It is to be understood that other deterministic negotiation protocols than the one described may be chosen for appointing a new wireless RF synchronization master.

Figure 3:
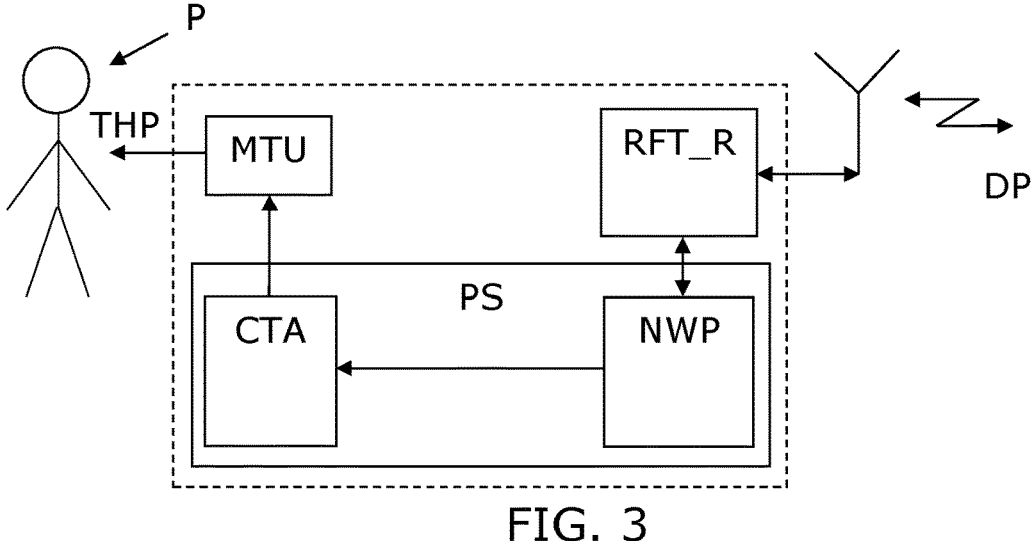
FIG. 3 illustrates a block diagram of a medical device embodiment.

FIG. 3 illustrates a medical device embodiment which is arranged to form part in a wireless TDMA network session and thus to receive wireless RF signals with data packets DP from connected sensor devices according the above description. The medical device has a medical therapy unit MTU arranged for medical active monitoring, and/or medical intervention, i.e. involving delivering some kind of therapy THP to a patient P. The medical device has a wireless RF transmitter and receiver unit RFT_R serving to receive data packets DP represented in an RF signal in accordance with a TDMA based network protocol as described above, so as to allow receipt of data packets DP with physical parameter data from sensor devices connected to the wireless TDMA network. A processor system PS is programmed to operate the wireless RF transmitter and receiver unit RFT_R according to the TDMA based network protocol NWP. Further, the processor system PS is connected to the medical therapy unit MTU so as to control at least one parameter of the medical therapy unit MTU in order to cause the medical therapy unit MTU to adapt the provided therapy THP in response to received physical parameter data DP from the wireless sensor device(s) on the TDMA network. The processor system executes a control algorithm which takes the received physical parameter data as input and determines one or more parameters which are applied to the medical therapy unit MTU.

The medical therapy unit may apply a medical therapy THP in the form of application of a gas, light, pressure, electric stimulation, or application of a chemical substance or the like. These can be adjusted in response to the physical measured parameters received from the wireless sensor devices to adapt the therapy THP to the needs of the patient P. The sensor data may sense body vital parameters of the patient P, and/or physical parameters related to the provided therapy THP, e.g. air pressure.

Figure 4:
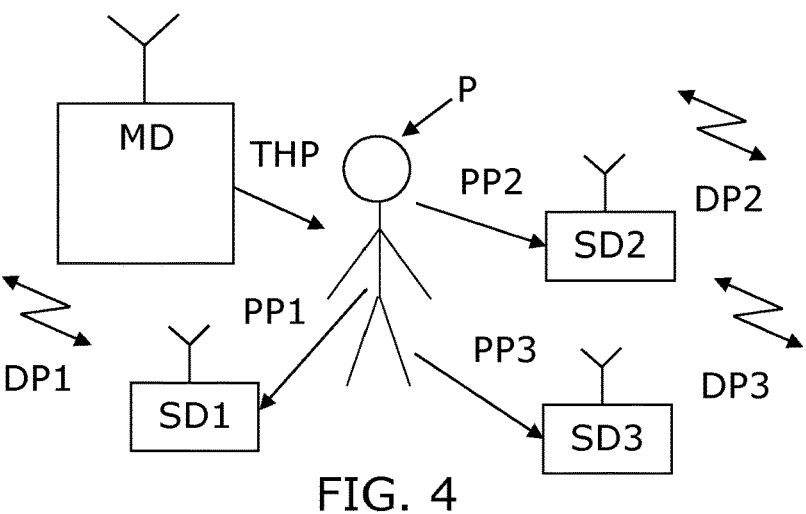
FIG. 4 illustrates a block diagram of a medical system embodiment.

FIG. 4 illustrates a medical system embodiment with a medical device MD as the embodiment described above in connection with FIG. 3, and three sensor devices SD1, SD2, SD3, corresponding to the embodiments described in connection with FIGS. 1 and 2. The sensor devices SD1, SD2, SD3 are arranged to measure different physical parameters PP1, PP2, PP3 related to the medical condition of the patent P and/or physical parameters related to a therapy THP applied to the patient P by the medical device MD. Data packets DP1, DP2, PD3 are communicated via a wireless RF based TDMA network from the sensor devices SD1, SD2, SD3 to the medical device MD.

Figure 5:
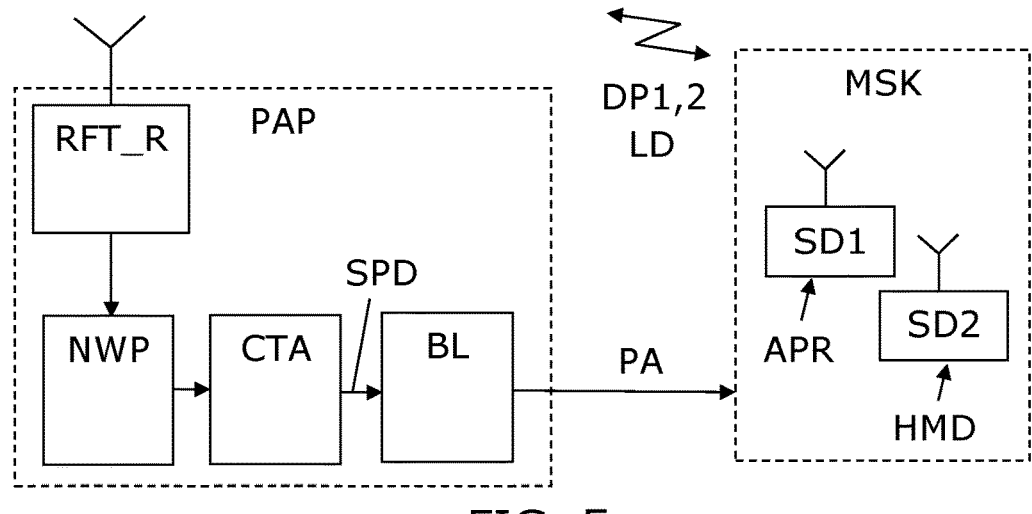
FIG. 5 illustrates a block diagram of a Positive Air Pressure device embodiment.

FIG. 5 illustrates a specific medical system embodiment wherein the medical device is a Positive Air Pressure device PAP, e.g. in the form or a Continuous Positive Air Pressure device (CPAP). Such CPAP system can be used for patients suffering from Apnea, since such patients can benefit substantially from forced delivery of air flow (or other breathing gases), i.e. pressurized air PA provided by a motorized blower BL, non-invasively to the airway via face mask MSK. A CPAP system can also used in invasive procedures under certain circumstances through a tracheal tube insertion procedure.

The application of CPAP requires precise calibration and control to ensure that the delivered airflow is in compliance with the patients' natural respiratory cycle. The face mask MSK provides a sealed contact between the mask flange or cushion and the skin, so as to enable maintaining the seal between 4 to 20 cm $H_2O$ of pressure, in 1.0 or 0.5 increments. The face mask may cover the nose, provide a cushion to the nose or prongs to the nose or a full mask that covers the nose and mouth and face. The mask MSK is connected to a ventilator or air pressure device through a tube, driven by the motorized blower BL.

An accurate picture of the patient's air flow to the mask MSK and general well-being is required for predictive delivery of positive air pressure to the patient. The mask MSK worn by the patient is primarily interfaced to a control system and an air blower BL within the PAP via an airflow hose. As illustrated, the speed SPD of the blower BL is controlled by a control algorithm CTA in the PAP, and the control algorithm CTA determines the appropriate speed SPD of the blower BL in response to data packets DP1, DP2 received via the wireless TDMA based network from two sensor devices SD1, SD2 positioned in or on the mask MSK. The first sensor device SD1 is arranged to sense an oscillatory pressure APR through the airflow hose as well as back pressure during the breathing cycles and transmits data packets DP1 accordingly to the PAP, which uses the APR data to determine the appropriate speed SPD of the air blower BL. The second sensor device SD2 has a humidity sensor to sense moisture or humidity HMD inside the mask MSK. The humidity data HMD are also transmitted in data packets DP2 to the PAP.

The sensor devices SD1, SD2 here serve to provide ultra-low latency wireless body area network to amalgamate multiple data points in order to generate a significantly higher positive predictive value to the pressure profile PA and duration through the airflow tube, compared to conventional means. Further sensors may be added to provide a detailed visibility into the patients' vital conditions, including but not limited to: snore sound, heart rate, blood pressure, as well as temperature. Together with the air pressure APR and humidity HMD mentioned, it can together provide pre-emptive data to spin up the blower BL and generate a gas pressure wave AP in anticipation of the next respiratory cycle of the patient P.

Further, the first sensor device SD1 may be capable of sensing a differential air pressure to determine possible leakage alongside the mask contact zone to the skin. The first sensor device SD1 may be programmed to determine a local decision based on measured pressures, that there is a leakage in the mask MSK.

This local decision LD made by the first sensor device SD1 is then transmitted to the PAP which can act accordingly. Thus, apart from delivering air pressure data APR to provide update info to the blower BL to increase or decrease speed SPD to control the air pressure AP, the first sensor device SD1 can itself perform a decision that can relieve the PAP from the task of checking for mask leakage based on raw pressure data. By such distributed local intelligent decisions, the PAP itself can be less complicated, and faster decisions can be obtained which can be important in a critical medical event.

The illustrated PAP may in have in the same unit as the blower BL a number of sensors at various positions in the air flow pressure parts and humidifier part serving to provide the pressurized air flow with a suitable humidity to be supplied via a tube to the mask MSK. These sensors may include such as: an airflow sensor, a humidity sensor, a pressure sensor, a thermistor sensing element, a magnetic sensor, and a thermostat.

In the face mask MSK separate sensors such as a heart rate sensor, a blood oxygen saturation sensor and a snore sound sensor may be present. Especially, all of the mentioned sensors can be connected to only one sensor device SD1 arranged physically in the mask, i.e. all data from the mentioned sensors can be transmitted wirelessly on the TDMA base network to the PAP from one single RF transmitter and receiver unit in the mask MSK. Still further sensors to be included, e.g. using separate sensor devices, such as for sensing chest movements, and abdomen movements which can also be communicated to the PAP.

Additional sensors such as those dedicated for measuring chest & abdomen movement may be added either as part of the configuration of the system or a separate on boarding process.

The system allows aggregate of interconnected sensor devices on a module that in turn report a multi-parametric data payload. Similarly, an aggregate of sensor devices in a system may operate semi-autonomously to report and function autonomously to provide various forms of localized decision making in addition to a more holistic picture with a detached sub-system such as a face mask.

The TDMA based network protocol allows high utilization of the available RF capacity, since sensors with different update rates and sampling rates can be incorporated without any loss of data capacity. The below example represents an embodiment of grouping of sensors and associated sampling rates, as a proposal.

Group W1
  Heart rate: sample rate 32-1,000 Hz, payload 16 bits.
  Blood pressure: sample rate 500-2,000 Hz, payload 12 bits.
  Blood oxygen saturation: sample rate 1-10 Hz, e.g. 5 Hz, payload 12 bits.
Group W2
  Abdominal movement: sample rate 50-200 Hz, payload 8 bits.
  Thoracic movement: sample rate 50-200 Hz, payload 8 bits.
  Leg movement: sample rate 50-200 Hz, payload 8 bits.
Group W3
  Snore sound: 2-8 kHz, e.g. 4 kHz, payload 16 bits.
  Temperature: 1 Hz, payload 8 bits.
  Humidity: 1 Hz, payload 8 bits.
  Airflow pressure: 500-2,000 Hz, e.g. 1 kHz, payload 8 bits.

Because the sensor data for some of the parameters may be transient in nature, it may make sense to analyze e.g. heart rate using power spectral density techniques. For continuous signals over time (such as blood pressure) a weighting factor may be applied to the overall value, so that in the event of a catastrophic occurrence the blower BL motor is able to ramp up rapidly and initiate emergency warning procedures as well.

Figure 6:
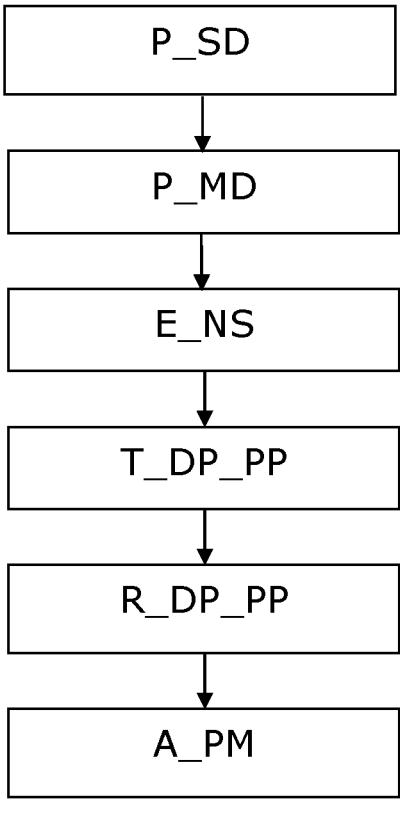
FIG. 6 illustrates steps of a method for controlling a medical device.

FIG. 6 illustrates steps of a method embodiment for controlling a medical device. First, providing P_SD one or more sensor devices as described above, next providing a medical P_MD device arranged to provide medical active monitoring or medical intervention and being arranged to receive data packets represented in an RF signal in accordance with a TDMA based network protocol. Next, establishing E_NS a wireless TDMA based network session between the sensor device and the medical device. Next, transmitting T_DP_PP, from the at least one sensor device, a data packet indicative of a sensed physical parameter represented in a wireless RF signal in accordance with the TDMA based network protocol. Next, receiving R_DP, by the medical device, the data packet via the wireless RF signal and determining the physical parameter represented therein. Finally, adapting A_PM at least one parameter of the medical active monitoring or medical intervention in response to the received physical parameter.

In a TDMA system, a frame is sub-divided into multiple slots, each of a specific duration. In preferred embodiments, each sensor device uses the time slot to either receive or transmit data. It is therefore critical that the system provisions to allow for slot, symbol and carrier synchronization.

A common assumption of TDMA based wireless ad hoc networks is the existence of a network wide frame synchronization. Such a mechanism is difficult to support in practice due to fading, propagation delays and signal attenuation. In the preferred TDMA network protocols, each sensor device, operating as wireless RF synchronization slave, uses a lookup table received from the wireless RF synchronization master that provides it with channel availability and access. The mechanism is preferably designed so that a sensor device may tag its payload and transmit immediately on any available channel without a lengthy negotiation process. A local time slot reference provided by the hardware clock tick of the sensor device itself that is in turn reinforced regularly by the wireless RF synchronization master. Inevitably, slots may be wasted when sensor devices switch time slot references. This restricts the spectral efficiency in comparison to a perfectly synchronized system, however given the system requirements for this application, the trade-off is a reasonable compromise in favor of flexibility and latency.

Figure 7:
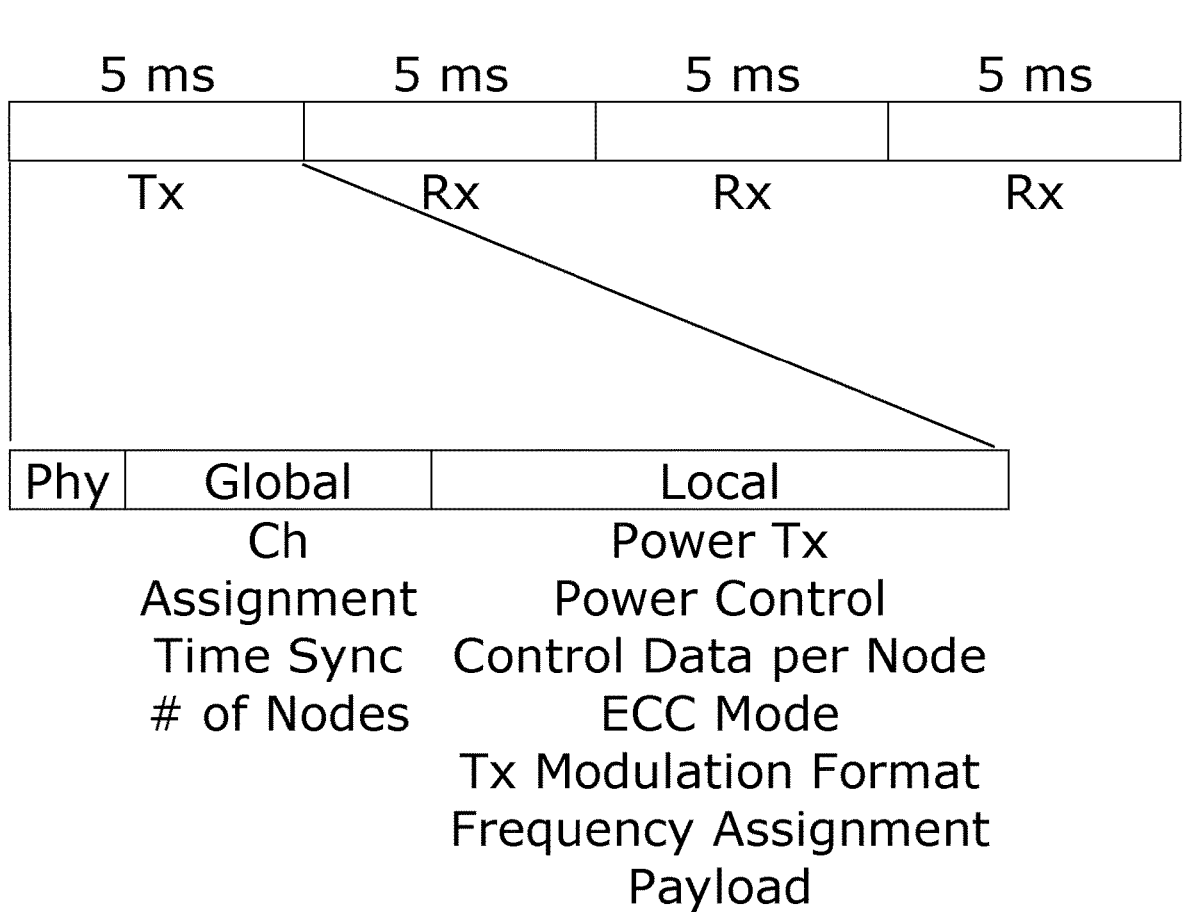
FIG. 7 illustrates a preferred frame structure for the wireless RF synchronization master, and FIG. 8. illustrates for the preferred frame structure transmission of data payload in 5 short time windows from sensor devices.

FIG. 7 illustrates for an example embodiment being a CPAP, the wireless RF synchronization master which, given the asymmetrical nature of the data communication requirements, is configured to transmit Tx data roughly 25% of the time only, in a preferred specific embodiment in 5 ms, including guard bands, and receive Rx data in the remaining 15 ms period in 5 ms periods. In the transmit Tx time window, the wireless RF synchronization master imposes the frame structure and timing constraints of the overall network topology. Especially, as shown, a Global field sets Channel Assignment, Time Synchronization, and Total number of nodes (devices). A local field sets: Transmit Power, Power control, Control data per node (device), Transmit Modulation format, Error Correction Code (ECC) mode, Frequency Assignment, and Payload.

The above example applies specifically for a CPAP, whereas for a robotic surgical device or an active prosthetic or a defibrillator the duty cycles maybe be chosen differently.

Figure 8:
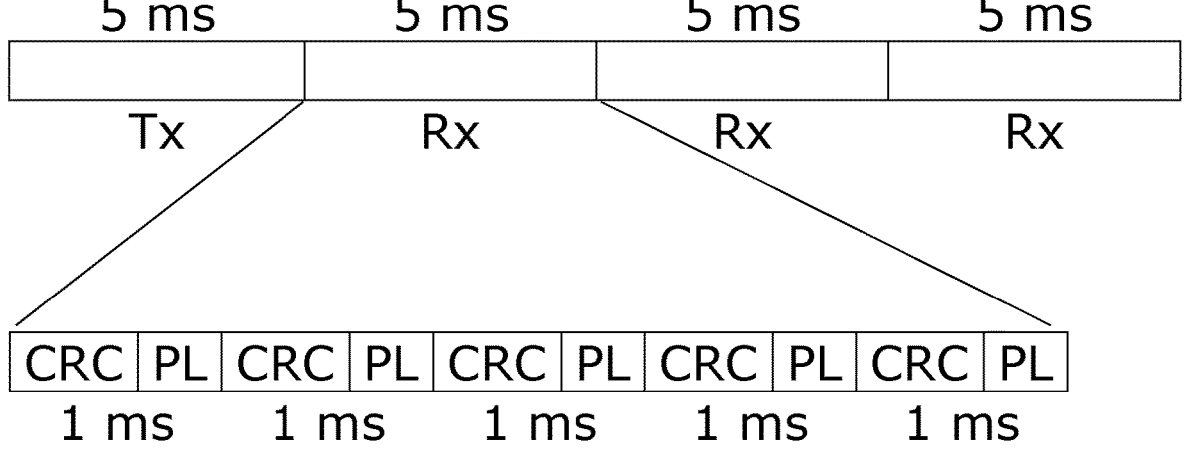

FIG. 8 shows again for the wireless RF synchronization master, the preferred one 5 ms transmit Tx time followed by three times 5 ms receive Rx time. Preferably, the wireless RF synchronization master transmits in every frame information on channel conditions and availability. The sensor device (slave) receives this and processes said information, and depending on channel availability, the sensor device can begin transmitting immediately in 1 ms chunks of payload data PL including CRC. This allows a sensor device to quickly transmit its data, therefore providing a very low latency.

In preferred embodiments, the TDMA based network supports a plurality of closely spaced RF carrier frequencies. The sensor device may be programmed to provide a background frequency scanning serving multiple purposes:

(a) Detecting timeslot and frequency positions with least interference.
  (b) Detecting the timeslot and frequency position of the master synchronization signal.
  (c) Discover communication from other devices in a network group.
  (d) Discover the presence of other network subgroups for potential rejoining.

The sensor devices may use two or more of the supported RF carrier frequencies for redundant data packet transmission in order to improve the rate of successful transmission. The selection of the two RF carrier frequencies for the redundant data transmission may be provided by means of measurement of RSSI or merely a measured RF signal level in the relevant frequency range.

To sum up, the invention provides a wireless sensor device for wireless transmission of sensed medical data to a medical monitoring and/or intervention device. The sensor device has a sensor element for sensing a physical parameter related to a body of a living person or animal. A wireless RF transmitter and receiver serves to transmit data packets with the sensed physical parameter, and to also receive data packets, in accordance with a TDMA based network proto- col.

A processor system controls operation of the wireless RF transmitter and receiver, including that the sensor device can operate as wireless RF synchronization master or slave, and the sensor device can negotiate according to a deterministic negotiation algorithm to appoint one of a plurality of wire- less RF devices connected to the TDMA based network as wireless RF synchronization master, if it is detected that no master is available. This allows a self-healing network, since one of a number of slave devices present in the network session can be appointed as a new master, thus even though the master device becomes out of range or is switched off. This provides a reliable and low latency wireless RF net- work for medical system, e.g. for a Continuous Positive Air Pressure device (CPAP) which can use sensed data from one or more sensor device to control its air blower to provide an appropriate air pressure.

Although the present invention has been described in connection with the specified embodiments, it should not be construed as being in any way limited to the presented examples. The scope of the present invention is to be interpreted in the light of the accompanying claim set. In the context of the claims, the terms "including" or "includes" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A sensor device comprising—at least one sensor ele- ment (SNS) arranged to sense a physical parameter (PP) related to a body of a living person (P) or animal or related to a medical therapy (THP) performed on the body,
    a wireless RF transmitter (RFT_R) arranged to transmit data packets (DP) indicative of the sensed physical parameter (PP) represented in an RF signal in accor- dance with a TDMA based network protocol,
    a wireless RF receiver (RFT_R) arranged to receive data (DP) packets represented in an RF signal in accordance with the TDMA based network protocol, and
    a processor system (PS) connected to control operation of the wireless RF transmitter and receiver (RFT_R) according to the TDMA based network protocol (NWP), being
    configured to operate as a wireless RF synchronization master or a wireless RF synchronization slave, and
    configured to communicate with other wireless RF devices connected to the TDMA based network via the wireless RF receiver and transmitter, and to negotiate with other wireless RF devices, whether to operate as a wireless RF synchronization master or a wireless RF synchronization slave, wherein said negotiation comprises a deterministic nego- tiation algorithm serving to appoint one of a plurality of wireless RF devices connected to the TDMA based network as wireless RF synchronization master, to ensure only one master for timing synchronization,
    wherein the negotiation algorithm causes devices con- nected to the TDMA based network to initiate a nego- tiation for appointing a new wireless RF synchroniza- tion master in case it is detected, that no wireless RF synchronization master is available in the TDMA based network session, and
    wherein the sensor device is programmed to, when appointed as wireless RF synchronization master, to impose TDMA frame structure and timing constraints of the TDMA based network, and wherein the sensor device is programmed to, when appointed as wireless RF synchronization master, to determine at least time synchronization of the TDMA frame structure.

2. The sensor device according to claim 1, wherein the deterministic negotiation algorithm causes the sensor device, if operating as a wireless RF synchronization master, to negotiate with one or more other wireless RF devices connected to the TDMA based network also operating as wireless RF synchronization master, so as to appoint only one wireless RF device to continue to operate as a wireless RF synchronization master, whereas the remaining wireless RF devices will switch to wireless RF synchronization slave operation.

3. The sensor device according to claim 1, wherein the processor system is programmed to operate as a wireless RF synchronization slave as a default mode of operation when entering a wireless TDMA network session.

4. The sensor device according to claim 1, wherein said physical parameter data comprises body vital parameter data for the living person or animal.

5. The sensor device according to claim 1, wherein said physical parameter data comprises one or more of: heart rate, blood pressure, blood oxygen saturation, abdominal movement, thoracic movement, leg movement, snore sound, body temperature, perspiration such as humidity, carbon dioxide exhalation, and tremor of a body part.

6. The sensor device according to claim 1, wherein said physical parameter data comprises one or more therapy relevant parameter data related to a medical therapy of the body.

7. The sensor device according to claim 1, wherein said physical parameter data comprises one or more of: an airflow pressure, an airflow rate, a temperature, a moisture or humidity measure, a measure of a gas mixture.

8. The sensor device according to claim 1, wherein the sensor device is programmed to process a sensed physical parameter sensed by the sensor element according to a decision algorithm in order to determine a decision in response to the sensed physical parameter.

9. The sensor device according to claim 8, wherein the sensor device is arranged to receive an RF signal from one or more wireless RF devices connected to the wireless TDMA based network and to receive further physical parameter data represented therein, and to process said received further physical parameter data according to the decision algorithm to determine the decision in response thereto, and wherein the sensor device is arranged to trans- mit data indicative of said decision represented in an RF signal via the TDMA based network.

10. The medical system according to claim 1, wherein the medical device comprises an Adaptive Positive Air Pressure device or a Continuous Positive Air Pressure device comprising a controllable air blower for delivering a controllable pressurized air to an airway of the living person or animal.

11. The sensor device according to claim 1, wherein the sensor device is arranged to, when operating as a wireless RF synchronization slave, to communicate directly with another sensor device operating as a wireless RF synchronization slave, without requiring communication relay by a wireless RF synchronization master.

12. A medical system comprising at least one sensor device according to claim 1, a medical device comprising at least one medical therapy unit arranged to provide one or both of: medical active monitoring, and medical intervention of a living person or animal, a wireless RF receiver arranged to receive data packets represented in an RF signal in accordance with a TDMA based network protocol, so as to allow receipt of data packets with physical parameter (PP) data from the at least one sensor device, a processor system connected to the wireless RF receiver and programmed to operate according to the TDMA based network protocol, and wherein the processor system is connected to the medical therapy unit so as to control at least one parameter of the medical therapy unit in order to cause the medical therapy unit to adapt the provided medical active monitoring or medical intervention in response to received physical parameter data from the at least one wireless sensor device.

13. The medical system according to claim 12, wherein the medical device comprises a ventilator device, such as an intensive care ventilator device, arranged to provide air to an airway of the living person or animal the in an automatic cycle or a semi-automatic cycle.

14. A method for controlling a medical device, providing at least one sensor device according to claim 1, providing a medical device arranged to provide medical active monitoring or medical intervention of a living person or animal, the medical device further comprising a wireless RF receiver arranged to receive data packets represented in an RF signal in accordance with a TDMA based network protocol, establishing a wireless TDMA based network session between the at least one sensor device and the medical device, transmitting, from the at least one sensor device, a data packet indicative of a sensed physical parameter represented in a wireless RF signal in accordance with the TDMA based network protocol, receiving, by the medical device, the wireless RF signal and determining the physical parameter represented therein, and adapting at least one parameter of the medical active monitoring or medical intervention in response to the received physical parameter.

\* \* \* \* \*